(12) United States Patent
Park et al.

(10) Patent No.: US 7,722,887 B1
(45) Date of Patent: May 25, 2010

(54) **DETOXIFIED MUTANTS OF *ESCHERICHIA COLI* HEAT-LABILE ENTEROTOXIN**

(75) Inventors: Eun Jeong Park, Sungnam-si (KR); Jang Seong Kim, Suwon (KR); Jihoon Chang, Seoul (KR); Jungsun Yum, Sungnam-si (KR); Soo-il Chung, Sungnam-si (KR)

(73) Assignee: Mogam Biotechnology Research Institute, Kyonggi-do (KR)

( * ) Notice: Subject to any disclaimer, the term of this patent is extended or adjusted under 35 U.S.C. 154(b) by 0 days.

(21) Appl. No.: 10/088,202

(22) PCT Filed: Sep. 15, 1999

(86) PCT No.: PCT/KR99/00555

§ 371 (c)(1),
(2), (4) Date: Mar. 15, 2002

(87) PCT Pub. No.: WO01/19998

PCT Pub. Date: Mar. 22, 2001

(51) Int. Cl.
*A61K 39/108* (2006.01)
*A61K 39/38* (2006.01)
*A61K 39/02* (2006.01)
*A61K 38/00* (2006.01)

(52) U.S. Cl. ............... 424/241.1; 424/184.1; 424/236.1; 424/257.1; 514/2; 530/300

(58) Field of Classification Search .................. None
See application file for complete search history.

(56) References Cited

FOREIGN PATENT DOCUMENTS

EP     0 620 850  B1  *  3/1999

OTHER PUBLICATIONS

Ellis (Vaccines, W.B. Saunders Company, 1988, Chapter 29).*
Boslego et al (Vaccines and Immunotherapy, Pergaman Press, 1991, Chapter 17).*
Park et al (Experimental and Molecular Medicine, Jun. 1999, vol. 31, No. 2, p. 101-107).*
Tommaso, et al.: *Infection and Immunity*, vol. 64, No. 3, pp. 974-979, Mar. 1996; "Induction of Antigen-Specific Antibodies in Vaginal Secretions by Using a Nontoxic Mutant of Heat Labile Enterotoxin as a Mucosal Adjuvant."
Marchetti, et al.: *Vaccine*, vol. 16, No. 1, pp. 33-37, 1998; "Protection against *Helicobacter pylori* Infection in Mice by Intragastric Vaccination with *H Pylori* Antigens is Achieved Using a Non-Toxic Mutant of *E. Coli* Heat-Labile Enterotoxin (LT) as Adjuvant.".
Verweij, et al.: *Vaccine*, vol. 16, No. 20, pp. 2069-2076, 1998; "Musosal Immunoadjuvant Activity of Recombinant *Escherichia Coli* Heat-Labile Enterotoxin and its B Subunit: Induction of Systemic IgG and Secretory IgA Responses in Mice by Intranasal Immunization with Influenza Virus Surface Antigen.".

* cited by examiner

*Primary Examiner*—Vanessa L. Ford
(74) *Attorney, Agent, or Firm*—Joseph H. Kim; JHK Law

(57) ABSTRACT

The present invention relates to detoxified and immunologically active proteins ("mutant LTs") having mutated amino acid sequences of heat-labile enterotoxin of *E. coli*, DNA sequences encoding the mutant LTs, recombinant expression vectors comprising the DNAs, recombinant microorganisms transformed with the recombinant expression vectors, process for preparing the mutant LTs and pharmaceutical application of the said protein as immunogenic antigens for vaccination and as adjuvants for anti-body production. In contrast to wild-type LT, the mutant LTs did not induce any toxic activities. The mutant LTs elicited high and comparable levels of anti-LT antibodies when delivered either intragastrically or intranasally, inducing systemic and local responses in serum and fecal extracts. Thus, they might be useful for the development of a novel diarrheal vaccine in humans and animals. In addition, the antibody production ability using mutant LTs as an adjuvant may be effective for prevention and treatment of various diseases.

6 Claims, 9 Drawing Sheets

DETOXIFIED MUTANTS OF *ESCHERICHIA COLI* HEAT-LABILE ENTEROTOXIN

CROSS REFERENCE TO OTHER APPLICATIONS

Figure 1:
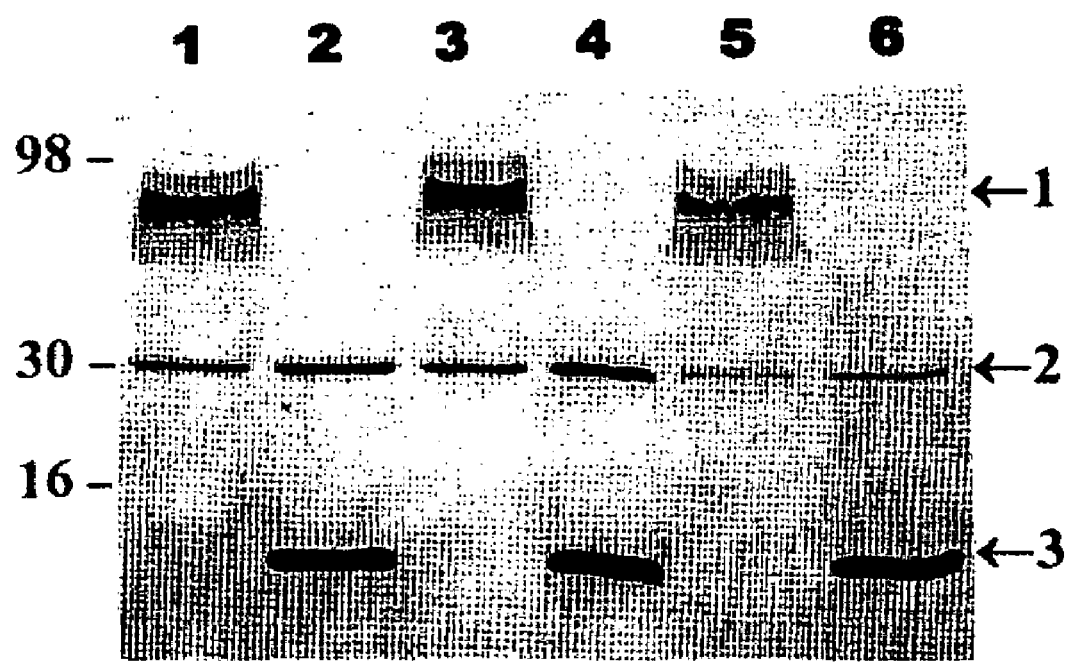
Figure 2:
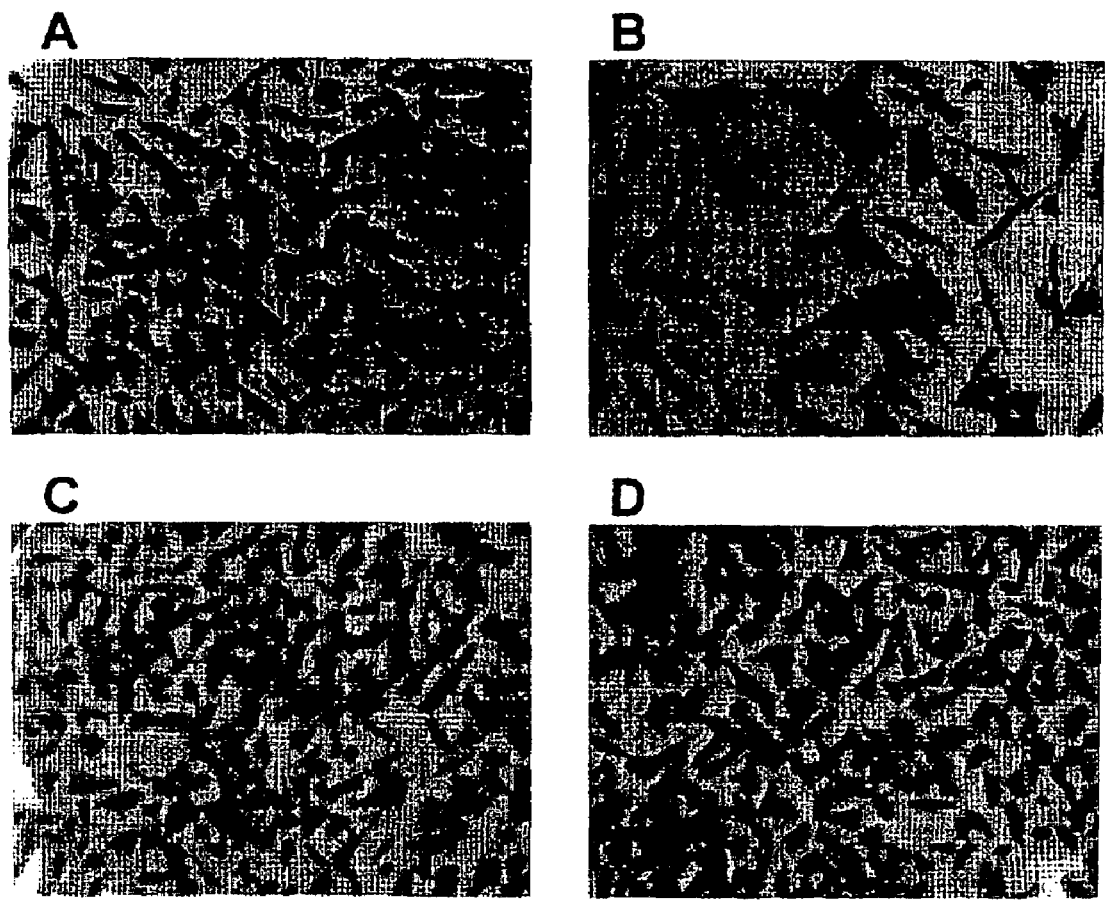

The present application is filed under 35 U.S.C. 371, and is the U.S. national phase application of PCT/KR99/00555, filed on Sep. 15, 1999.

BACKGROUND OF THE INVENTION

1. Field of the Invention

The present invention relates to detoxified and immunologically active proteins ("mutant LTs"), more specifically, to mutant LTs having mutated amino acid sequences of heat-labile enterotoxin of *E. coli,* DNA sequences encoding the mutant LTs, recombinant expression vectors comprising the DNAs, recombinant microorganisms transformed with the recombinant expression vectors, process for preparing the mutant LTs and pharmaceutical application of the said proteins as immunogenic antigens for vaccination and as adjuvants for antibody production.

2. Description of the Prior Art

Enterotoxigenic *Escherichia coli* ("ETEC") strain causes diarrheal disease in humans and animals due to production of toxin such as heat-labile enterotoxin ("LT") (see: Spangler, B. D., Microbiol. Rev., 56:622-647(1992)). LT is a multimeric protein composed of two functionally distinct domains: an enzymatically active A subunit ("LTA") of ~30,000 daltons with ADP-ribosylating activity, and a pentameric B subunit ("LTB") of ~11,600 daltons that contains GM1 (momosialoganglioside) receptor-binding site (see: Bäckström, M. et al., Mol. Microbiol., 24:489-497(1997)). Upon thiol reduction, the A subunit dissociates into two polypeptide chains, i.e., A1 (Mr, 23,000 daltons) and A2 (Mr, 6,000 daltons) (see: Tsuji, T. et al., J. Biol. Chem., 260:8552-8558(1985); Grant C. C. R. et al., Infect. Immun., 62:4270-4278(1994)). The A1 subunit, in particular, intoxicates eucaryotic cells by catalyzing ADP-ribosylation of Gs, a GTP-binding protein that regulates the levels of the second messenger cAMP (see: Guerrant, R. L. et al., Infect. Immun., 10:320-327(1974); Field, M. et al., N. Engl. J. Med., 321:800-806(1989)). The resulting increase in cAMP level causes secretion of water and electrolytes into the small intestine through interaction with two cAMP-sensitive ion transport mechanisms including (i) NaCl co-transport across the brush border of villous epithelial cells and (ii) electrogenic $Na^+$-dependent $Cl^-$ secretion by crypt cells (see: Guidry, J. J. et al., Infect. Immun., 65:4943-4950(1997)).

Both the cholera toxin ("CT") from *Vibrio cholerae* and heat-labile enterotoxin from ETEC belong to the most potent mucosal adjuvants and immunogens known to date by oral and other mucosal routes, via which most of antigens are unable to induce immune responses (see: Jackson, R. J. et al., Infect. Immun., 61:4272-4279(1993); Takahashi, I. et al., J. Infect. Dis., 173:627-635(1996)). However, their toxicities have precluded their clinical use in humans (see: Douce, G. et al., Proc. Natl. Acad. Sci., USA, 92:1644-1648(1995)). One approach to overcome the problem of toxicity is the generation of genetically detoxified derivatives of LT (see: Lobet, Y. et al., Infect. Immun., 59:2870-2879(1991); Dickson, B. L. and Clements, J. D., Infect. Immun., 63:1617-1623(1995)) and CT (see: Fontana, M. R. et al., Infect. Immun., 63:2356-2360(1995); Yamamoto, S. et al., Proc. Natl. Acad. Sci., USA, 94:5267-5272(1997b)) by site-directed mutagenesis of amino acids which are located on the β-strand that constitutes the 'floor' of NAD-binding cavity.

The most important factor for immunogenicity is shown to be the ability to bind to the receptor on eucaryotic cell (see: Nashar, T. O. et al., Proc. Natl. Acad. Sci., USA, 93:226-230 (1996)). In fact, a non-binding mutant of the B subunit of LT was found to be non-immunogenic (see: Guidry, J. J. et al., Infect. Immun., 65:4943-4950(1997)). In addition, another group found that the ADP-ribosylating activity is unnecessary for immunogenicity because nontoxic derivatives of LT obtained by site-directed mutagenesis of the A subunit retained the immunological properties of the wild-type LT (see: Pizza, M. et al., J. Exp. Med., 180:2147-2153(1994)).

The attempt to define the role of ADP-ribosylating activity in adjuvanticity of LT has generated conflicting results. For example, it was reported that a nontoxic derivative of LT (LTE112K) when co-administered with keyhole limpet hemocyanin (KLH) by an oral route in mice, lacked the adjuvant properties, thus suggesting that the adjuvanticity of LT is linked to its ADP-ribosylating activity (see: Lycke, N. et al., Eur. J. Immunol., 22:2277-2281(1992)). However, more recently, the adjuvant activity of the LTE112K was found to be identical to that of the LT holotoxin when delivered with influenza virus surface antigen by an intranasal route (see: Verweij, W. R et al., Vaccine, 16:2069-2076(1998)). On the other hand, other investigators showed that another LT derivatives, LTK63, lacking enzymatic activity and toxicity was still able to elicit antibody responses against the co-administered antigen in mice immunized orally, intranasally, or intravaginally (see: Di Tommaso, A. et al., Infect. Immun., 64:974-979 (1996); Giuliani, M. M. et al., J. Exp. Med., 187:1123-1132 (1998); Marchetti, M. et al., Vaccine, 16:33-37(1998)).

Under the circumstances, the present inventors, based on the findings that detoxified LT derivatives may induce antibody responses, tried to explore an efficient immunogenic antigen and mucosal adjuvant for vaccination, which can be applied for the development of a mucosal vaccine as well as a novel diarrheal vaccine for humans and animals.

SUMMARY OF THE INVENTION

In accordance with the present invention, the inventors have made an effort to develop detoxified and immunologically active proteins ("mutant LTs") by the site-directed mutagenesis of heat-labile enterotoxin (LT) of *E. coli*. The inventors cloned full length DNA coding for the LT, mutated the A subunit by site-directed mutagenesis and constructed expression vectors comprising the DNAs of mutated LT and recombinant microorganisms transformed with the recombinant expression vectors. Further, the inventors found that the recombinant mutant LTs can be applied as an active ingredient for diarrheal vaccine and adjuvant for mucosal vaccine.

The first object of the invention is, therefore, to provide detoxified and immunologically active proteins which have mutated amino acid sequences of heat-labile enterotoxin of *E. coli.*

The second object of the invention is to provide DNA sequences encoding the said mutant LTs.

The third object of the invention is to provide recombinant expression vectors comprising the said DNAs.

The fourth object of the invention is to provide recombinant microorganisms transformed with the said recombinant expression vectors.

The fifth object of the invention is to provide a process for preparing recombinant mutant LTs from the said microorganisms.

The sixth object of the invention is to provide a diarrheal vaccine comprising an active ingredient of mutant LT.

The seventh object of the invention is to provide a novel use of the mutant LT as an adjuvant for mucosal vaccine.

BRIEF DESCRIPTION OF THE INVENTION

The above and the other objects and features of the present invention will become apparent from the following description given in conjunction with the accompanying drawings, in which:

FIG. 1 is a photograph showing SDS-PAGE of a wild-type and mutant LTs produced and isolated from recombinant *E. coli*.

FIG. 2 is photographs showing the changes in CHO-K1 cell morphology after treatment with wild-type or mutant LTs.

FIG. 3 is a photograph showing ADP-ribosyltransferase activity of wild-type LT, LTS63Y and LT⊿ 110/112 analyzed by SDS-PAGE followed by autoradiography.

FIG. 4 is a graph showing the amount of intracellular cAMP of CHO cells measured by an enzyme immunoassay system after treatment with wild-type or mutant LTs.

FIG. 5 is graphs showing anti-LT secretary IgA, serum IgG and IgA antibody responses on intragastric or intranasal immunization.

FIG. 6 is graphs showing anti-urease secretary IgA, serum IgG and IgA antibody responses on intragastric immunization.

FIG. 7 is graphs showing anti-urease secretary IgA, serum IgG and IgA antibody responses on intranasal immunization.

FIG. 8A is a graph showing anti-urease serum IgG subclass antibody responses on intragastric immunization.

FIG. 8B is a graph showing anti-urease serum IgG subclass antibody responses on intranasal immunization.

DETAILED DESCRIPTION OF THE INVENTION

The present inventors first isolated a DNA fragment including heat-labile enterotoxin (LT) gene from enterotoxigenic *E. coli* K88ac strain of porcine origin and thus cloned into pBluescript KS (−) vector to generate pBlueKS-/rLT for site-directed mutagenesis. Site-directed mutagenesis was performed on single-stranded DNA of pBlueKS-/rLT vector. As a result, two vectors that have mutated DNA sequences encoding amino acids of proposed ADP-ribosyltransferase active center of LT were generated: the first one is 'pBlueKS-/LTS63Y' wherein serine residue at position 63 of LT is substituted with tyrosine; and, the other one is 'pBlueKS-/LT⊿ 110/112' wherein glutamic acid residues at positions 110 and 112 are deleted.

Amino acids at positions 58 to 72 are shown to be folded in a β-strand followed by α-helix, which form the NAD-binding site and amino acids $Arg^7$, $His^{44}$, $Ser^{61}$ $Glu^{110}$ and $Glu^{112}$ have been shown to be important for enzymatic activity. Up to date, the modified residues of the LTA subunit are $Arg^7$, $Ser^{63}$, $Glu^{110}$, $Glu^{112}$ or $Ala^{72}$.

The inventors have substituted $Ser^{63}$, the essential amino acid for NAD-binding and catalytic activity of LT, with Tyr residue having a bulky side chain of phenolic ring. Thus, it was expected to efficiently block NAD-binding in slightly modified LT structure. The inventors have also deleted $Glu^{110}$ and $Glu^{112}$ in LTA subunit which are important for enzymatic activity, and have studied for immunogenicity to LT itself and immune-eliciting property against coadministered antigens. The double deletion mutant of the invention was expected to completely eliminate, enzymatic activity of LT.

In describing the mutant LTs of the present invention, LTS63Y is employed to mean mutated LT in which serine residue at position 63 is substituted with tyrosine; and, "LT⊿ 110/112" is employed to mean mutated LT in which glutamic acid residues at positions 110 and 112 of LT are deleted, respectively.

pBlueKS-/LTS63Y and pBlueKS-/LT⊿ 110/112, were transformed into *E. coli* Top 10F'. Each of the transformants thus prepared was designated as '*Escherichia coli* Top 10F'-pBlueKS-/LTS63Y' and '*Escherichia coli* Top 10F'-pBlueKS-/LT⊿ 110/112' and deposited with the Korean Collection for Type Cultures (KCTC) located at KRIBB #52, Oun-dong, Yusong-gu, Taejon 305-333, Republic of Korea, an international depository authority as accession Nos. KCTC 0648BP and KCTC 0649BP, respectively.

*E. coli* Top 10F' transformed with either pBlueKS-/LTS63Y or pBlueKS-/LT⊿ 110/112 was grown in LB broth containing 100 μg/ml of ampicillin and the mutant LTs were purified from the cultures using immobilized D-galactose column and FPLC Superdex 200 column.

Since the mobilities of mutant LTs were identical to those of the wild-type LT on SDS-PAGE analysis, the molecular weight of the mutant LT subunits were presumed to be identical to those of wild-type LT. These results suggest that mutant LTs consisting of A and B subunits retain the $AB_5$ conformation similar to wild-type LT.

The ability of mutant LTs to induce morphological changes in cultured Chinese hamster ovary-K1 (CHO-K1) cells (ATCC, USA) was tested. The morphological changes in the CHO-K1 cells were used to detect the toxic activity of mutant LTs (see: Grant, C. C. R. et al., Infect. Immun., 62:4270-4278 (1994)). As little as 100 ng/ml of LT induced longitudinal growth of approximately 90% of the CHO-K1 cells, a response previously shown to be dependent upon adenylate cyclase-induced increases in cAMP (see: Guerrant, R. L. et al., Infect. Immun., 10:320-327(1974)). However, the cells treated with each of the mutant LT at the level of 10 μg/ml showed no morphological changes of the CHO-K1 cells.

ADP-ribosyltransferase activity was determined as the ability to catalyze the transfer of labeled ADP-ribose from [adenylate-$^{32}$P]NAD to the 41 kDa G protein in CHO-K1 membrane (see: Locht, C. et al., Infect. Immun., 55:2546-2553(1987)). In general, A1 subunit of LT is known to catalyze ADP-ribosylation of the membrane-bound substrate G proteins. When membrane proteins from CHO-K1 cells were incubated with wild-type LT in the presence of [adenylate-$^{32}$P]NAD, it specifically ADP-ribosylated the Mr 41,000 proteins, which correspond to the α subunits of the GTP binding Gs protein. In contrast, no ADP-ribosylation of this protein was detected in reaction mixtures incubated with the same amounts of LTS63Y or LT⊿ 110/112. This result was identical to that of the negative control treated without toxins. Therefore, the substitution of $Tyr^{63}$ for $Ser^{63}$ or deletion of $Glu^{110}$ and $Glu^{112}$ in A1 subunit appeared to cause changes in structural integrity of NAD binding crevice that may be important for enzymatic activity of LT.

In addition, the levels of cAMP were determined in CHO cells treated with CT, LT, or mutant LTs. The addition of CT or LT caused about 10-fold higher levels of cAMP production than that of untreated cultures. On the other hand, changes in cAMP levels in LTS63Y- or LT⊿ 110/112-treated cells were barely detectable. These data showed that the presence of A subunit of wild-type LT (accurately LTA1 subunit) is necessary for an increase in the intracellular cAMP concentration and the mutant derivatives, LTS63Y and LT⊿ 110/112, devoid of enzymatic activity, are unable to form cAMP.

The enterotoxicity experiments of mutant LTs examined using a mouse ileal loop test strongly indicate that the mutant LTs possess negligible enterotoxicity in vivo.

In the immunogenic ability of mutant LTs, the mice immunized with LTS63Y or LT$\Delta$110/112 contained high and comparable levels of anti-LT antibodies in sera and fecal extracts compared with those immunized with wild-type LT. Moreover, both of the intragastric and intranasal immunizations using mutant LTs could be an effective method for inducing antibody responses of vaccination.

The ability of mutant LTs to act as a mucosal adjuvant was assessed by intragastric immunization in mice. LT$\Delta$110/112 was effective as a mucosal adjuvant on intragastric immunization by inducing high levels of mucosal and systemic antibody responses to the coadministered antigens such as *H. pylori* whole cell lysate or urease. The ability of mutant LTs to function as a mucosal adjuvant was also assessed by intranasal immunization in mice. Intranasal administration of LTS63Y demonstrated the sensitiveness in inducing mucosal immunigenecity and adjuvanticity. Mice immunized intranasally by coadministration of urease antigen and LTS63Y showed strong mucosal and systemic anti-urease responses including urease-specific secretary IgA, serum IgG and IgA antibodies.

The present invention is further illustrated in the following examples, which should not be taken to limit the scope of the invention.

EXAMPLE 1

Expression and Purification of Mutant LTs

EXAMPLE 1-1

Plasmid Construction and Mutagenesis

A 1.5 Kb BamHI DNA fragment including LT gene from enterotoxigenic *E. coli* K88ac strain of porcine origin was cloned into pBluescript KS(−) vector (Stratagene, USA). The resulting vector, designated as pBlueKS-/rLT, was used for site-directed mutagenesis.

Site-directed mutagenesis was performed on single-stranded DNA prepared from *E. coli* CJ236 transformed with pBlueKS−/rLT according to the method of MutanK kit (Takara Biomedicals, Japan). The sequence of oligonucleotides used for the substitution and deletion of amino acids were 5'-ATATGATGACGGATATGTTTCCACTTAC-CTTAGTTTGAGAAGTGCTCACTTG-3' (SEQ ID NO:1) and 5'-AGGCGTATACAGCCCTCACCCATATCAG-GTTTCTGCGTTAGG TGGAATACCAT-3' (SEQ ID NO:2), respectively. As a result, serine residue at position 63 was substituted with tyrosine and glutamic acid residues at positions 110 and 112 were deleted, respectively.

These residues are in proposed ADP-ribosyltransferase active center of LT and their substitutions or deletions have been shown to inactivate ADP-ribosyltransferase activity and enterotoxicity (see: Domenighini, M. et al., Mol. Microbiol., 14:41-50(1994)).

Amino acids at positions 58 to 72 are shown to be folded in a β-strand followed by α-helix, which form the NAD-binding site and amino acids $Arg^7$, $His^{44}$, $Ser^{61}$ $Glu^{110}$ and $Glu^{112}$ have been shown to be important for enzymatic activity. Up to date, the modified residues of the LTA subunit are $Arg^7$ (to Lys), $Ser^{63}$ (to Lys), $Glu^{110}$ (to Asp), $Glu^{112}$ (to Asp or Lys) or $Ala^{72}$ (to Arg) (see: Lobet, Y. et al., Infect. Immun., 59:2870-2879(1991); Fontana, M. R. et al., Infect. Immun., 63:2356-2360(1995); Di Tommaso, A. et al., infect. Immun., 64:974-979(1996); Douce, G. et al., Infect. Immun., 63:2821-2828 (1997); Marchetti, M. M. et al., Vaccine, 16:33-37(1998); Tsuji, T. et al., FEBS Letters, 292:319-321(1991); Lycke, N. et al., Eur. J. Immunol., 22:2277-2281(1992); Verweij, W. R. et al., Vaccine, 16:2069-2076(1998); Giuliani, M. M. et al., J. Exp. Med., 187:1123-1132(1998)).

The substitution of $Ser^{63}$, the essential amino acid for NAD-binding and catalytic activity of LT, with Tyr residue having a bulky side chain of phenolic ring was expected to efficiently block NAD-binding in slightly modified LT structure. Deletion of Glu110 and Glu112, which are located at the putative ADP-ribosyltransferase active center was also expected to completely eliminate enzymatic activity of LT.

The changes of DNA sequences were confirmed using Sequenase Version 2.0 sequencing kit (Amersham Life Science, USA) and each of mutants thus prepared was designated as 'pBlueKS-/LTS63Y' and 'pBlueKS-/LT$\Delta$110/112', respectively.

EXAMPLE 1-2

Expression and Purification of the Recombinant mutant LTs pBluescript KS(−) vectors containing the mutant LT gene which comprises the 160 bp 5'-noncoding region, 1.2 kb coding region and 197 bp 3'-noncoding region, pBlueKS-/LTS63Y and pBlueKS-/LT$\Delta$110/112, were transformed into *E. coli* Top 10F'(Invitrogen, USA). Each of the transformants thus prepared was designated as '*Escherichia coli* Top 10F'-pBlueKS-/LTS63Y' and '*Escherichia coli* Top 10F'-pBlueKS-/LT $\Delta$110/112' and deposited with the Korean Collection for Type Cultures (KCTC) located at KRIBB #52, Oun-dong, Yusong-gu, Taejon 305-333, Republic of Korea, an international depository authority as accession Nos. KCTC 0648BP and KCTC 0649BP, respectively.

*E. coli* Top 10F' transformed with either LTS63Y or LT $\Delta$110/112 was grown in LB broth containing 100 μg/ml of ampicillin and the mutant LTs were purified from the cultures. The cells were harvested by centrifugation, resuspended in TEAN buffer (50 mM Tris-HCl, pH 7.5, 0.2M NaCl, 1 mM EDTA and 3 mM $NaN_3$), and lysed with a microfluidizer (Microfluidics Corporation, USA). The lysates were clarified by centrifugation and then filtered using 0.45 μm membrane (Micro Filtration Systems, Japan) prior to chromatography on an immobilized D-galactose column (Pierce, USA) (see: Uesaka, Y. et al., Microb. Pathog. 16:71-76(1974)). Bound proteins were eluted with 0.3M galactose in TEAN buffer. Holotoxin ($AB_5$) was separated from the free B-subunit pentamer by size exclusion chromatography using FPLC Superdex 200 column (Pharmacia, Sweden).

The homogeneity of LTS63Y and LT$\Delta$110/112 was confirmed by SDS-polyacrylamide gel electrophoresis (see: FIG. 1). In FIG. 1, lanes 1 and 2 represent wild-type LTs; lanes 3 and 4, LTS63Ys; and, lanes 5 and 6, LT$\Delta$110/112s, respectively, and the arrow 1 is a position of LT holotoxins and LTB subunit pentamers; arrow 2, LTA subunit; and, arrow 3, LTB subunit monomer. Each lane received 10 μg of the proteins and samples in lanes 2, 4 and 6 were heated to 95° C. for 5 min in the presence of β-mercaptoethanol, while samples in lanes 1, 3 and 5 were loaded without denaturation by heating and adding β-mercaptoethanol. When the purified mutant LTs were analyzed without denaturation, two protein bands appeared: one band with the size of 70-100 kDa corresponding to the holotoxin and LTB pentamers; and, the other band with the size of about 30 kDa corresponding to the LTA subunit. When the purified mutant LTs were boiled for 5 min with β-mercaptoethanol, the holotoxins were dissociated into two bands of about 30 and 11 kDa, corresponding to the A and B subunits of LT, respectively. Since the mobilities of mutant LTs were identical to those of the wild-type LT, the molecular weight of the mutant LT subunits were presumed to be identical to those of wild-type LT.

These results suggest that the innate structure of the A subunit associated with pentameric B subunits of LT is not affected by substitution of tyrosine for Ser$^{63}$ or deletion of Glu$^{110}$ and Glu$^{122}$ residues on NAD-binding pocket. Moreover, it was demonstrated that the binding ability of the B subunit of mutant LTs to $G_{M1}$ ganglinoside was similar to that of the normal B subunit using a $G_{M1}$-ELISA, and mutant LTs were reacted with anti-LT antibody in Western blot analysis. These results imply that mutant LTs retain the $AB_5$ conformation similar to wild-type LT.

EXAMPLE 2

Enzymatic and Biologic Characterization of Mutant LTs

EXAMPLE 2-1

Cell Elongation Assay

The ability of mutant LTs to induce morphological changes in cultured Chinese hamster ovary-K1 (CHO-K1) cells (ATCC, USA) was tested as described previously (see: Guerrant, R. L. et al., Infect. Immun., 10:320-327(1974); Grant, C. C. R. et al., Infect. Immun., 62:4270-4278(1994)). CHO-K1 cells were incubated for 24 hr as monolayer cultures in minimal essential medium alpha (MEM-α)(Gibco-BRL, USA) supplemented with 10% fetal bovine serum (FBS) in humidified and 5% $CO_2$ atmosphere at 37° C. The cells were washed once with Hanks's balanced salt solution (HBSS) (Sigma, USA) and then incubated with 0.1% trypsin for 5 min. After centrifugation, they were washed once, and then resuspended in the growth medium. To each well of a 48-well tissue culture plate, the same numbers of CHO-K1 cells ($10^4$ in 200 μl volume per well) were allowed to adhere for 4 hr prior to the addition of the toxin dilutions and then incubated in humidified and 5% $CO_2$ atmosphere at 37° C. for 24 hr. The cells were then washed with phosphate-buffered saline (PBS), fixed with methanol, and stained with 0.04% Trypan Blue Solution (Gibco-BRL, USA). After staining, the cells were washed, air dried, and analyzed for morphological changes by light microscopy.

The morphological changes in the CHO-K1 cells were used to detect the toxic activity of mutant LTs (see: Grant, C. C. R. et al., Infect. Immun., 62:4270-4278(1994)). As little as 100 ng/ml of wild-type LT induced longitudinal growth of approximately 90% of the CHO-K1 cells, a response previously shown to be dependent upon adenylate cyclase-induced increases in cAMP (see: Guerrant, R. L. et al., Infect. Immun., 10:320-327(1974)). However, the cells treated with mutant LTs at the level of 10 μg/ml showed no morphological changes of the CHO-K1 cells (see: FIG. 2 and Table 1). In FIG. 2, A shows toxin-untreated CHO-K1 cells; B, CHO-K1 cells treated with 100 ng/ml of wild-type LT; C, CHO-K1 cells treated with 10 μg/ml of LTS63Y; and, D, CHO-K1 cells treated with 10 μg/ml of LT⊿ 110/112, respectively.

TABLE 1

Comparison of biologic and enzymatic activities of wild-type LT, LTS63Y and LTΔ110/112

| Toxin assessed | Cell elongation[a] | Ileal loop test[b] |
|---|---|---|
| PBS | 10%< | negative |
| Wild-type LT | 90%> at 100 ng | positive at 100 ng |
| LTS63Y | 10%< at 10 μg | negative at 100 μg |
| LTΔ110/112 | 10%< at 10 μg | negative at 100 μg |

[a]$10^4$ of CHO-K1 cells were cultured with 100 ng of wildtype LT or 10 μg of each mutant LT for 24 hr and a positive toxin effect in the CHO-K1 cells was defined as elongation of >20% of the cells according to published criteria (see: Guerrant, R. L. et al., Infect. Immun. 10:320-327 (1974))
[b]The enterotoxicity of mutant LTs was examined using on ileal loop test, where mice were anesthetized, and 100 μl of PBS containing 100 ng of wild-type LT or 100 μg of each mutant LT was injected into an ileal loop. Loops were examined 18 hr later and the ratio of fluid to length was defined, as positive when the ratio was >40 μl/cm (see: Fujita, K. et al., J. Infect. Dis. 125: 647-655 (1972))

EXAMPLE 2-2

ADP-ribosyltransferase Activity Test

For the preparation of crude membranes, CHO-K1 cells were maintained in monolayer culture by serial passage in MEM-α medium supplement with 10% FBS (see: Locht C. et al., Infect. Immun., 55:2546-2553(1987)). The cells were detached from the flask, washed once in PBS (pH 7.2) and then lysed in a homogenizer (Weaton, USA). The supernatant from these lysates was collected following centrifugation at 1,000×g for 20 min and further centrifuged at 18,000×g for 7 min to obtain microsomal or membrane pellets. The washed membrane pellet was resuspended in 50 mM Tris-HCl (pH8.0) at a concentration of 1 mg of protein per ml and stored at −70° C. until use.

ADP-ribosyltransferase activity was determined as the ability to catalyze the transfer of labeled ADP-ribose from [adenylate-$^{32}$P]NAD to the 41 kDa G protein in CHO-K1 membrane (see: Locht, C. et al., Infect. Immun., 55:2546-2553(1987)). Reaction mixtures (100 μl) containing 32 μM [adenylate-$^{32}$P]NAD(2 μCi) (NEN, USA), 50 mM Tris-HCl (pH 8.0) containing 10 mM thymidine, 100 mM ATP, 20 mM DTT, 100 μM GTP, 50 μg of CHO-K1 membrane proteins, and 10 μg of wild-type or mutant LTs were incubated at 37° C. for 30 min. Reactions were terminated by the addition of 1 ml of ice-cold 50 mM Tris-HCl (pH 8.0) and the membranes were sedimented by centrifugation (15,000×g, 7 min) at 4° C. The membrane pellet was resuspended in ice-cold Tris-HCl (pH 8.0) and sedimented once more by centrifugation before being solubilized in 50 μl of electrophoresis sample buffer (67 mM Tris-HCl, pH 6.8, 2% SDS, 0.03% bromophenol blue, and 10% glycerol) containing 5% β-mercaptoethanol. The samples were heated to 95° C. for 5 min and then analyzed by SDS-PAGE and autoradiography.

In general, the A1 subunit of LT is capable of binding NAD and catalyzing the ADP-ribosylation of membrane-bound Gs, a GTP-binding regulatory protein associated with adenylate cyclase (see: Spangler, B. D., Microbiol. Rev., 56:622-647 (1992)). The consequence is a sharp increase in cAMP production resulting in excessive accumulation of salts and water in the intestinal lumen (see: Field, M. et al., N. Engl. J. Med., 322:800-806(1989)). The A subunit of LT is known to catalyze ADP-ribosylation of the membrane-bound substrate G proteins.

FIG. 3 shows ADP-ribosyltransferase activity of LT, LTS63Y and LT⊿ 110/112 analyzed by SDS-PAGE in a 12.5% gel followed by autoradiography. In FIG. 3, lane 1 represents a reaction mixture incubated without toxins; lane 2, with 10 μg of wild-type LT; lane 3, with 10 μg of LTS63Y; and, lane 4, with 10 μg of LTΔ 110/112, respectively, and the arrow denotes the position of the Mr-41,000 band corresponding to the Gs protein.

Figure 3:
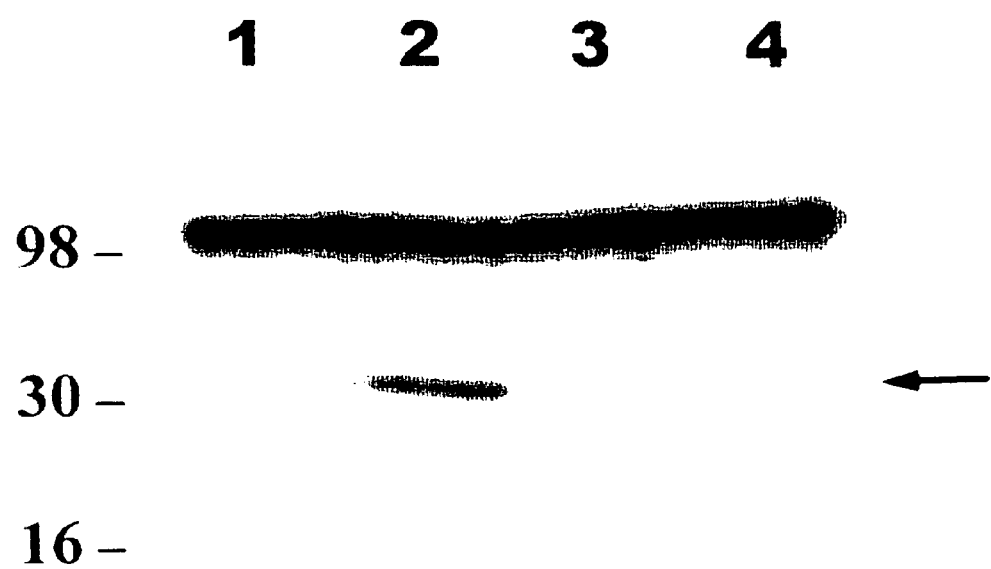

As shown in FIG. 3, when 50 μg of membrane proteins from CHO-K1 cells were incubated with wild-type LT in the presence of [adenylate-$^{32}$P]NAD, it specifically ADP-ribosylated the Mr-41,000 proteins, which correspond to the α subunits of the GTP binding Gs proteins. In contrast, no ADP-ribosylation of this protein was detected in reaction mixtures incubated with the same amounts of LTS63Y or LTΔ 110/112. This result was identical to that of the negative control treated without toxins in lane 1. Therefore, the substitution of Tyr$^{63}$ for Ser$^{63}$ or deletion of Glu$^{110}$ and Glu$^{112}$ in A subunit did cause changes in structural integrity of NAD binding crevice that may be important for enzymatic activity of LT.

EXAMPLE 2-3

Measurement of Intracellular cAMP Accumulation

CHO cells (ATCC, USA) were maintained in MEM-α medium supplemented with 10% FBS in a 24-well plate at a concentration of $5×10^4$ cells per well, grown to near confluency, and incubated in MEM-α containing FBS and 1 mM 3-isobutyl-1-methylxanthine (IBMX) for 30 min prior to addition of toxins (see: Grant, C. C. R. et al., Infect. Immun., 62:4270-4278(1994)). Either cholera toxin (CT), cholera toxin B subunit (CTB), trypsin-activated wild-type LT, LTS63Y, or LTΔ 110/112 was added to each well and the plates were incubated for 18 h. The cells were washed three times with PBS and intracellular cAMP was extracted by adding 200 μl of 50 mM HCl to each well and placing the plates in −70° C. deep freezer for 20 min. cAMP was measured with a Biotrak cAMP enzyme immuno-assay (EIA) system (Amersham Life Science, USA) according to the manufacturer's instructions.

Figure 4:
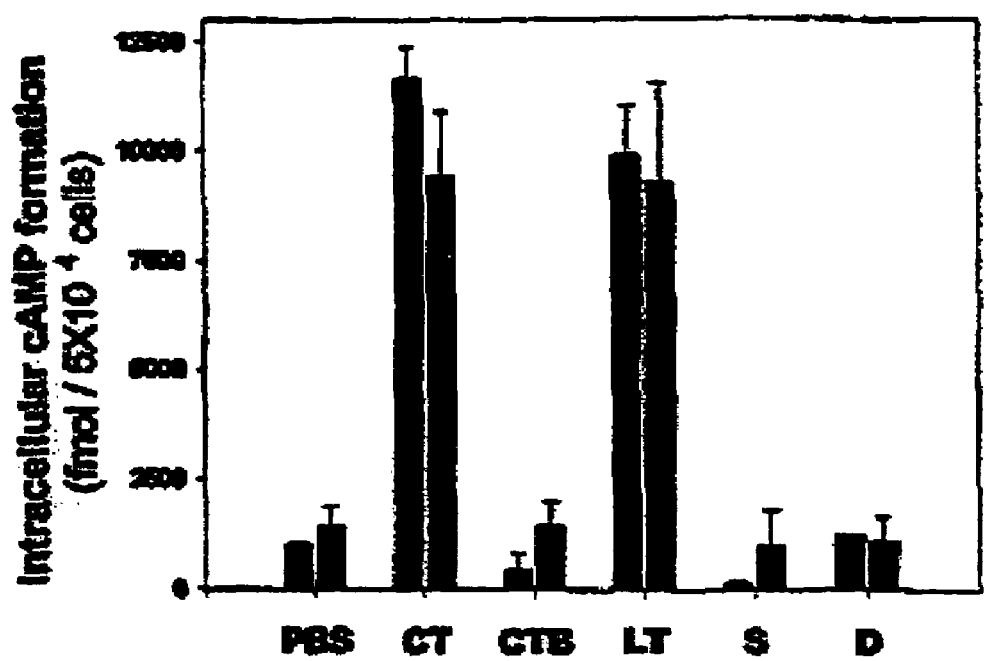

As a result, the levels of cAMP were determined in CHO cells treated with CT, CTB, LT, LTS63Y, or LTΔ 110/112 (see: FIG. 4). As shown in FIG. 4, the addition of CT or LT to reach a concentration of 50 ng/ml caused about 10-fold higher levels of cAMP production than those of untreated cultures. On the other hand, cAMP formation in cultures treated with CTB, LTS63Y or LTΔ 110/112 was undetectable even at a concentration as high as 5 μg/ml. In FIG. 4, 'S' and 'D' denote LTS63Y and LTΔ 110/112, respectively, and the gray bars represent treatments of 500 ng of CT or LT and 5 μg of CTB, S or D; and, black bars, 50 ng of CT or LT and 500 ng of CTB, S or D. Results are shown as mean titers and error bars indicate standard deviations from the mean.

These data showed that the presence of wild-type LTA subunit (accurately LTA1 subunit) is necessary for an increase in the intracellular cAMP concentration and the mutant derivatives, LTS63Y and LTΔ 110/112, devoid of enzymatic activity, are unable to form cAMP.

EXAMPLE 2-4

Assessment of Toxicity using Mouse Ileal Loops

The enterotoxicity of mutant LTs was examined using a mouse ileal loops test (see: Yamamoto, S. et al., J. Exp. Med., 185:1203-1210(1997)). Groups of mice were anesthetized, and different doses of each toxin were injected into ileal loops (LT, 100 ng or 1 μg per mouse; and, mLT, 10 μg or 100 μg per mouse) of individual mice. The mice were sacrificed 18 hr after the injection, and the fluid content of the ileal loops was determined; values of more than 40 μl cm were considered positive (indicative of toxicity).

One hundred nanogram of wild-type LT induced significant fluid accumulation in small intestine, while no fluid accumulation was observed in the loop treated with thousand-fold higher levels (100 μg) of mutant LTs (see: Table 1). These data strongly indicate that the mutant LTs possess negligible enterotoxicity in vivo.

EXAMPLE 3

Immunological Characterization

EXAMPLE 3-1

Mucosal Immunogenicities of mLTs

Figure 5:
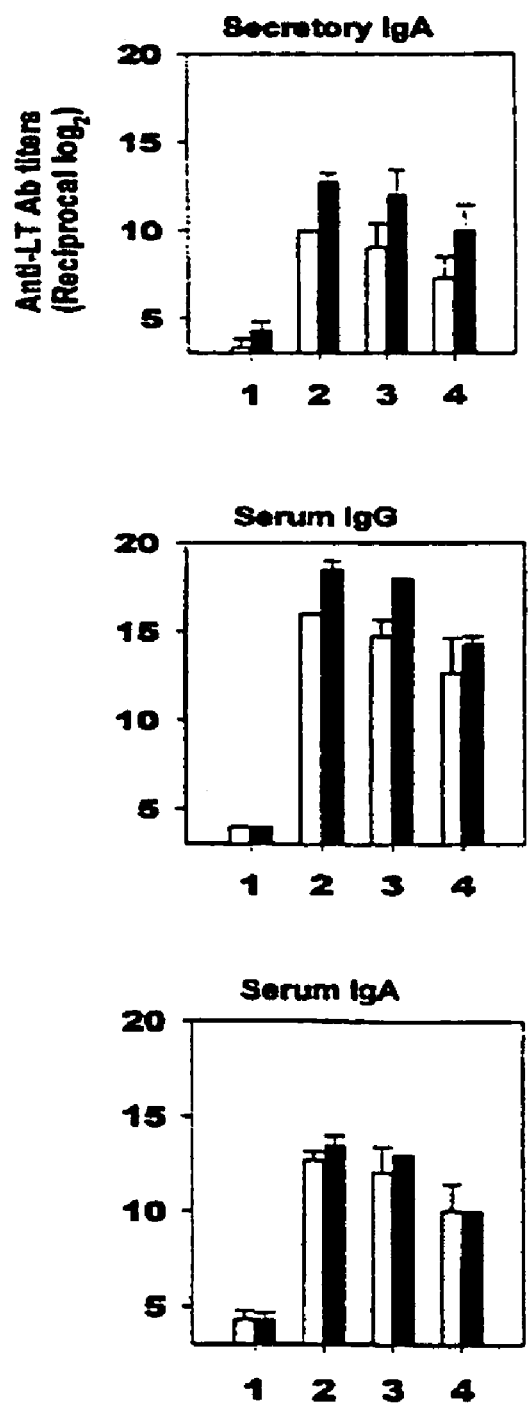

Six-week-old female Balb/c mice were purchased from Charles River (Japan). The mucosal immunogenicities of LTS63Y and LTΔ 110/112 were tested via two immunization routes. Groups of mice were immunized intragastrically with 25 μg of LTS63Y or LTΔ 110/112 four times on days 0, 7, 14 and 21 or intranasally with 2 μg of LTS63Y or LTΔ 110/112 on days 0, 7 and 14 (see: Takahashi, I. et al., J Infect. Dis., 173:627-635(1996)). The control groups received PBS alone. The serum and fecal antibody titers to LT were determined using samples prepared on day 7 following the last immunization (see: FIG. 5). FIG. 5 shows anti-LT secretary IgA, serum IgG and IgA antibody responses on intragastric (white bar) or intranasal (black bar) immunization, where 1 represents PBS treatment; 2, wild-type LT treatment; 3, LTS63Y treatment; 4, LTΔ 110/112 treatment.

As shown in FIG. 5, the mice immunized with LTS63Y or LTΔ 110/112 contained high and comparable levels of anti-LT antibodies in sera and fecal extracts compared with those immunized with wild-type LT. The LTS63Y was slightly more immunogenic than LTΔ 110/112 on both intragastric and intranasal administration. On the other hand, titers of anti-LT in the serum or fecal extracts of mice intranasally immunized with wild-type or mutant LTs were slightly higher than those observed in mice intragastrically administered. Intranasal immunization offers several advantages compared with other immunization route: lower doses of proteins are required to induce antibody responses, which means lower cost for vaccine production (see: Yamamoto, S. et al., Proc. Natl. Acad. Sci., USA, 94:5267-5272(1997)). When administered intranasally, only 6% of the quantity of mutant LT used in intragastric immunization was required to elicit slightly higher levels of secretary IgA responses and this dose also effectively induced systemic IgG and IgA antibody responses. Thus, intranasal immunization using mutant LT could be an effective method for vaccination in humans and animals.

EXAMPLE 3-2

Mucosal Adjuvanticity of Mutant LTs

To test a mucosal adjuvanticity, mice were immunized either intragastrically by 125 μg of *H. pylori* urease together with 25 μg of LTS63Y or LTΔ 110/112 on days 0, 7, 14 and 21 or intranasally by 20 μg of the same antigen together with 2 μg of LTS63Y or LTΔ 110/112 as an adjuvant on days 0, 7 and 14. Fecal extracts and serum samples were collected on day 7 following the last immunization and the appearance of either mucosal or systemic antibody responses was monitored using ELISA.

LT- and urease-specific antibodies were measured with a $G_{M1}$ capture enzyme-linked immunosorbent assay ($G_{M1}$-

ELISA) and direct ELISA, respectively, as described previously (see: Spiegel, S. J. Cell. Biochem., 42:143-152(1990); Douce, G. et al., Infect. Immun., 65:2821-2828(1997)). Plates were coated with 150 ng of $G_{M1}$ (Sigma, USA) per well of a 96-well EIA/RIA plate (Costar, USA) for a $G_{M1}$-capture ELISA, and then incubated at 37° C. for 1 hr. Plates were washed three times with PBS containing 0.05% Tween 20 ("PBST") and blocked with 2.5% skim milk (Difco, USA) in PBST at 37° C. for 1 hr. After washing with PBST three times, 100 ng of wild-type LT was added into wells and plates were incubated for 1 hr at 37° C. and washed three times with PBST. In case of a direct ELISA, plates were coated with 1 µg of urease per well incubated for 1 hr at 37° C. with horseradish peroxidase (HRP)-conjugated anti-mouse antibodies specific for mouse immunoglobulinG (IgG) (1:5000), IgA (1:2000) (KPL, USA) or IgG1, IgG2a or IgG2b (1:2000) (Biosource, USA). After washing six times with PBST, bound antibody was visualized by addition of 3,3'5'5'-tetramethylbenzidine (TMB). The absorbance at 450 nm was determined and ELISA titers were recorded as the highest dilution of serum which gave an absorbance value above the level meaesured in preimmune samples.

Mucosal Adjuvanticity of LTS63Y and LT△110/112 by Intragastric Immunization

Figure 6:
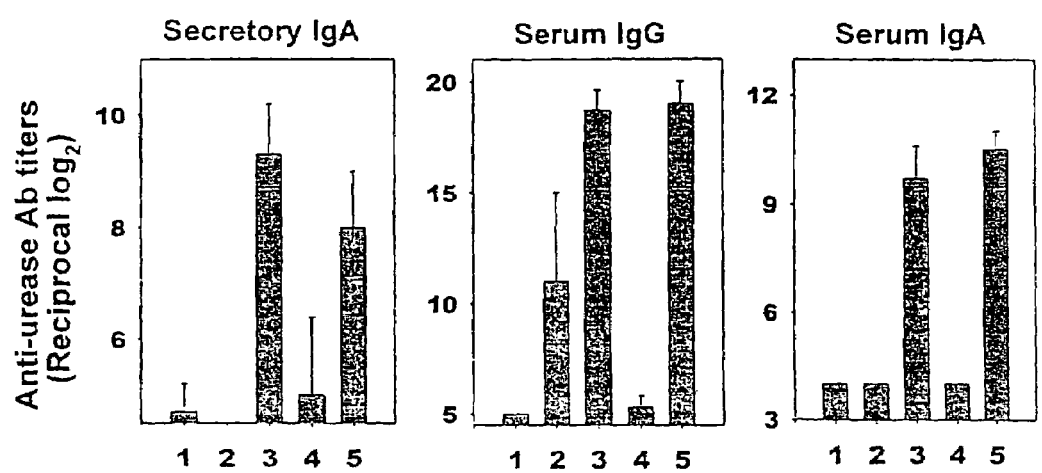

The ability of mutant LTs to act as a mucosal adjuvant was assessed by intragastric immunization in mice (see: FIG. 6: 1, PBS treatment; 2, 125 µg urease treatment; 3, 125 µg urease and 25 µg LT treatment; 4, 125 µg urease and 25 µg LTS63Y treatment; 5, 125 µg urease and 25 µg LT△110/112 treatment).

As shown in FIG. 6, mice immunized intragastrically with *H. pyroli* urease alone showed no significant levels of antibodies to the antigen. Mice immunized by coadministration of urease and LT△110/112 produced high levels of urease antibody responses comparable to those immunized with wild-type LT, while mice immunized by coadministration of the antigen and LTS63Y showed no significant sero-conversion. Altering the dose of LT△110/112 to 10 or 125 µg did not cause any change in the immune response to urease. LTS63Y did not show any significant adjuvanticity to the urease, even when 125 µg was coadministered with the urease.

To test the adjuvanticity of LT△110/112 with other antigens, whole cell lysate of *H. pylori* was used as an antigen and it was observed that LT△110/112 also induced antibody responses to whole cell lysate. These data suggest that LT△110/112 effectively functions as a mucosal adjuvant on intragastric immunization by inducing strong mucosal and systemic antibody responses to coadministered antigens such as *H. pylori* whole cell lysate or urease.

Figure 8A:
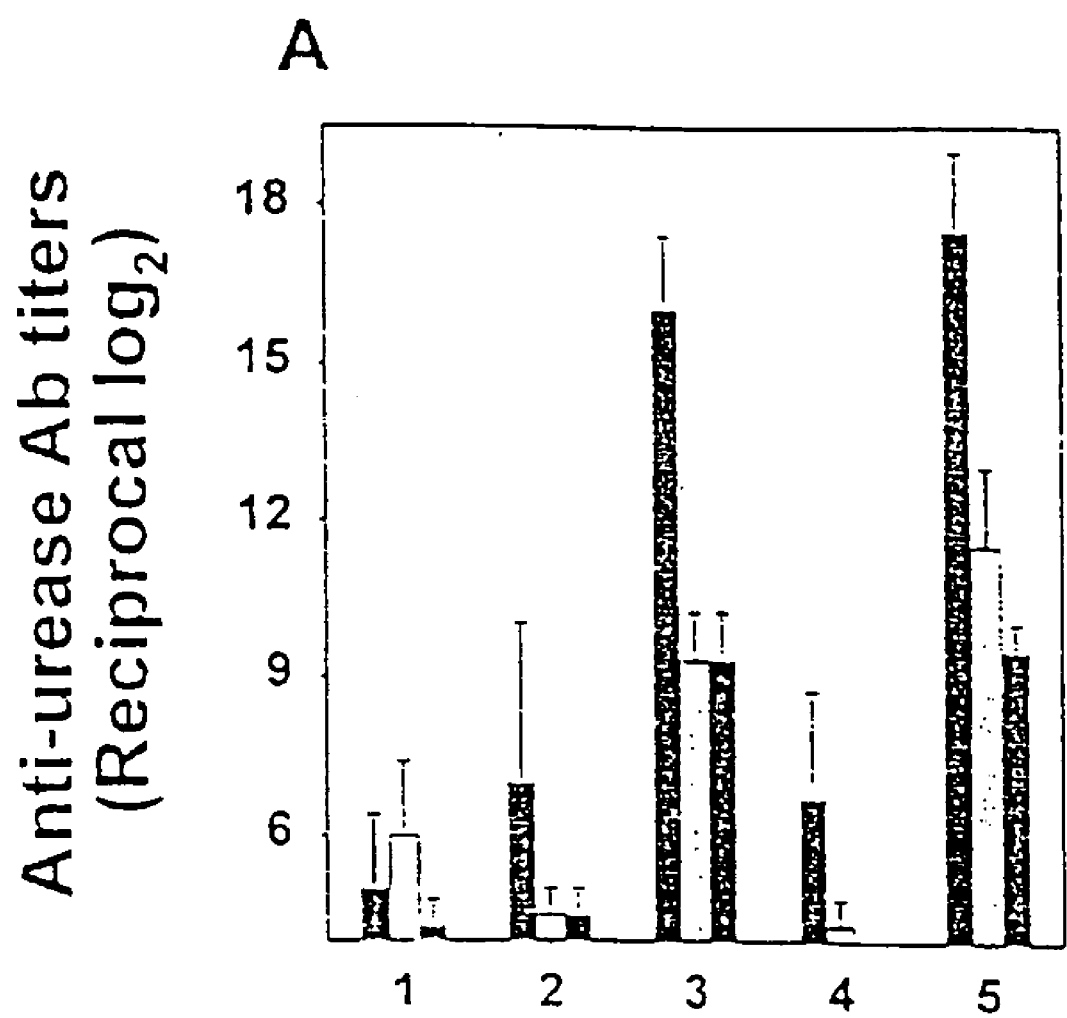

To further assess the immunologic response induced by LT△110/112 following intragastric immunization, IgG subclass responses were determined by ELISA (see: FIG. 8A: 1, PBS treatment; 2, 125 µg urease treatment; 3, 125 µg urease and 25 µg LT treatment; 4, 125 µg urease and 25 µg LTS63Y treatment; 5, 125 µg urease and 25 µg LT△110/112 treatment).

As shown in FIG. 8A, urease antibody responses enhanced by LT△110/112 were largely restricted to IgG1 (gray bars), rather than IgG2a (white bars) or IgG2b (black bars) subclass antibody in sera, and similar antibody patterns were observed using wild-type LT as an adjuvant.

Generally, CT elicits adjuvant responses by inducing antigen-specific CD4+ T cells secreting interleukin 4 (IL-4), IL-5, IL-6 and IL-10 that correlated directly with serum IgG1 and IgG2b subclass responses in mice orally immunized with protein Ag and CT as adjuvant (see: Marinaro. M. et al., J. Immunol., 155:4621-4629(1995). It was reported that mutant CT (S61F), despite lack of ADP-ribosyltransferase activity with resultant cAMP induction, elicits serum IgG1 and IgG2b subclass Ab responses when administrated intranasally (see: Yamamoto, S. et al., Proc. Natl. Acad. Sci., USA, 94:5267-5272(1997) or subcutaneously (see: Yamamoto, S. et al., J. Exp. Med., 185:1203-1210(1997). On the other hand, oral immunization with LT promotes IgG1, IgG2a and IgG2b, which are supported by a mixed CD4+ Th1- and Th2-type responses associated with IFN-γ, IL-4, IL-5, IL-6 and IL-10 production (see: Takahashi, I. et al., J. Infect. Dis., 173:627-635(1996). In the results of present invention, intragastric administration of LT△110/112 or wild-type LT as an adjuvant induced predominant IgG1 Ab responses as shown in FIG. 8A. This result is not consistent with the typical IgG subclass responses induced by wild-type LT and rather resembles the responses induced by CT activating CD4+ Th2-type cells (see: Marinaro, M. et al., J. Immunol., 155: 4621-4629(1995). In contrast, LTS63Y induced IgG1, IgG2a and IgG2b antibody responses to *H. pylori* urease on intranasal immunization. The similar result is also observed by wild-type LT eliciting IgG1, IgG2a and IgG2b subclass responses, which are supported by a mixed CD4+ Th1- and Th2-type response (see: Takahashi, I. et al., J. Infect. Dis., 173:627-635 (1996)). Therefore, the mutant LTs of this invention, LTS63Y and LT△110/112, induced distinct IgG subclass responses, depending on immunization routes.

Mucosal Adjuvanticity of LTS63Y and LT△110/112 by Intranasal Immunization

Figure 7:
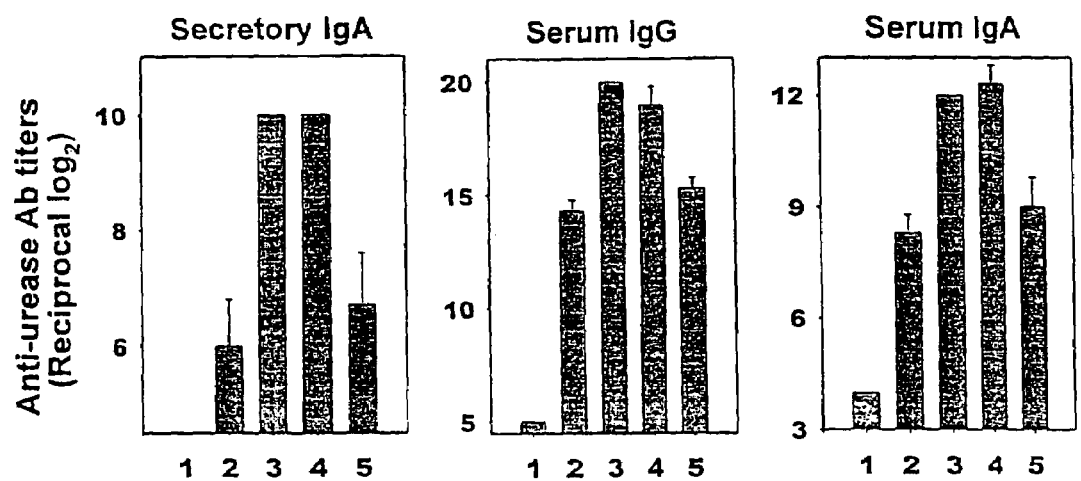

The ability of mutant LTs to function as a mucosal adjuvant was also assessed by intranasal immunization in mice. Intranasal administration of wild-type or mutant LTs demonstrated the sensitiveness in inducing mucosal immunigenecity and adjuvanticity (see: FIG. 7: 1, PBS treatment; 2, 20 µg urease treatment; 3, 20 µg urease and 2 µg wild-type LT treatment; 4, 20 µg urease and 2 µg LTS63Y treatment; 5, 20 µg urease and 2 µg LT△110/112 treatment).

Mice immunized intranasally by coadministration of urease antigen and LTS63Y showed high levels of mucosal and systemic anti-urease responses including urease-specific secretary IgA, serum IgG and IgA antibodies, which were equivalent to the responses observed when wild-type LT was used as an adjuvant. However, mice immunized by coadministration of urease and LT△110/112 showed lower level of antibodies to urease, similar to those levels induced by urease alone. When 0.2 µg of LTS63Y was used, antibody responses to urease in both fecal extracts and sera were lower by a factor of approximately 10, but when 6 µg of LTS63Y was used, no increase in antibody responses to urease was induced.

Figure 8B:
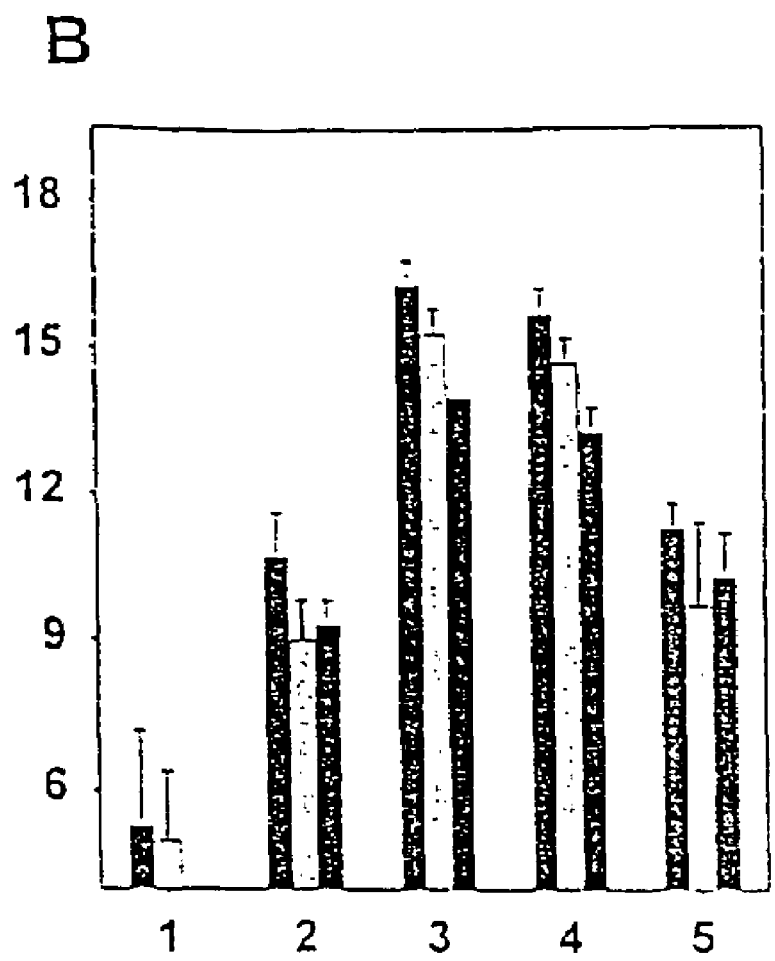

In addition, as shown in FIG. 8B, LTS63Y induced IgG1 (gray bars), IgG2a (black bars) and IgG2b (white bars) subclass antibody responses to *H. pylori* urease, and these results were quite different from those IgG subclass responses (predominant IgG1) resulted from the intragastric immunization with the mutant LT△110/112(see: FIG. 8B: 1, PBS treatment; 2, 20 µg urease treatment; 3, 20 µg urease and 2 µg LT treatment; 4, 20 µg urease and 2 µg LTS63Y treatment; 5, 20 µg urease and 2 µg LT△110/112 treatment). Therefore, the mutant LTs of this invention, LTS63Y and LT△110/112 induced district IgG subclass responses, depending on immunization routes.

As described above, the mutant LTs of this invention have shown different abilities to act as mucosal adjuvant according to the route of administration. This suggests that different mutant forms of LT may require different immunization routes for adequate adjuvanticity, and that specific immunization route may elicit specific mechanisms of up-regulation of immune responses, independent of cAMP levels. Thus, selection of the route of immunization may be critical for determining the mucosal adjuvant activity of mutant LTs. Mucosal vaccines delivered into the nasal tract provide several advantages. For example, lower doses of antigen and adjuvant are required to induce effective antibody responses when compared to intragastric immunization, which can decrease the cost of vaccination.

As clearly illustrated and demonstrated as above, the present invention provides detoxified and immunologically active proteins (mutant LTs). The mutant LTs was expressed from recombinant expression vectors, pBlueKS-/LTS63Y and pBlueKS-/LT⊿110/112 that contain mutated DNA sequences encoding amino acids in the ADP-ribosyltransferase active center. In contrast to wild-type LT, both of the LTS63Y and LT⊿10/112 did not induce any toxic activities. Both of the mutants elicited high and comparable levels of anti-LT antibodies when delivered either intragastrically or intranasally, inducing systemic and local responses in serum and fecal extracts. Thus, they might be useful for the development of a novel diarrheal vaccine in human and animals. In addition, the antibody production ability using LTS63Y and LT⊿110/112 as adjuvants against *H. pylori* urease may be effective for prevention and treatment of various diseases. The adjuvant activity of these mutants might be very useful to develop an effective mucosal vaccine component.

What is claimed is:

1. A detoxified and immunologically active heat-labile enterotoxin protein of *Escherichia coli*, wherein the serine residue at position 63 is substituted with tyrosine or amino acid residues at positions 110 and 112 are deleted.

2. A detoxified and immunologically active heat-labile enterotoxin protein having the amino acid sequence of SEQ ID NO.3.

3. A detoxified and immunologically active heat-labile enterotoxin protein having the amino acid sequence of SEQ ID NO.5.

4. A mucosal adjuvant comprising an active ingredient of the detoxified and immunologically active heat-labile enterotoxin protein of claim 1.

5. The detoxified and immunologically active heat-labile enterotoxin protein of claim 1, wherein serine residue at position 63 is substituted with tyrosine.

6. The detoxified and immunologically active heat-labile enterotoxin protein of claim 1, wherein glutamic acid residues at positions 110 and 112 are deleted.

* * * * *

SEQUENCE LISTING

```
<160> NUMBER OF SEQ ID NOS: 6

<210> SEQ ID NO 1
<211> LENGTH: 52
<212> TYPE: DNA
<213> ORGANISM: Artificial sequence
<220> FEATURE:
<223> OTHER INFORMATION: Primer
<220> FEATURE:
<221> NAME/KEY: primer_bind
<222> LOCATION: (1)..(52)

<400> SEQUENCE: 1
atatgatgac ggatatgttt ccacttacct tagtttgaga agtgctcact tg          52

<210> SEQ ID NO 2
<211> LENGTH: 53
<212> TYPE: DNA
<213> ORGANISM: Artificial sequence
<220> FEATURE:
<223> OTHER INFORMATION: Primer
<220> FEATURE:
<221> NAME/KEY: primer_bind
<222> LOCATION: (1)..(53)

<400> SEQUENCE: 2
aggcgtatac agccctcacc catatcaggt ttctgcgtta ggtggaatac cat         53

<210> SEQ ID NO 3
<211> LENGTH: 382
<212> TYPE: PRT
<213> ORGANISM: Escherichia coli
<220> FEATURE:
<221> NAME/KEY: SIGNAL
<222> LOCATION: (1)..(18)

<400> SEQUENCE: 3
```

Met Lys Asn Ile Thr Phe Ile Phe Phe Ile Leu Leu Ala Ser Pro Leu
1               5                   10                  15

Tyr Ala Asn Gly Asp Arg Leu Tyr Arg Ala Asp Ser Arg Pro Pro Asp
                20                  25                  30

Glu Ile Lys Arg Ser Gly Gly Leu Met Pro Arg Gly His Asn Glu Tyr
            35                  40                  45

Phe Asp Arg Gly Thr Gln Met Asn Ile Asn Leu Tyr Asp His Ala Arg
        50                  55                  60

Gly Thr Gln Thr Gly Phe Val Arg Tyr Asp Asp Gly Tyr Val Ser Thr
65                  70                  75                  80

```
Tyr Leu Ser Leu Arg Ser Ala His Leu Ala Gly Gln Ser Ile Leu Ser
                85                  90                  95

Gly Tyr Ser Thr Tyr Tyr Ile Tyr Val Ile Ala Thr Ala Pro Asn Met
            100                 105                 110

Phe Asn Val Asn Asp Val Leu Gly Val Tyr Ser Pro His Pro Tyr Glu
        115                 120                 125

Gln Glu Val Ser Ala Leu Gly Gly Ile Pro Tyr Ser Gln Ile Tyr Gly
    130                 135                 140

Trp Tyr Arg Val Asn Phe Gly Val Ile Asp Glu Arg Leu His Arg Asn
145                 150                 155                 160

Arg Glu Tyr Arg Asp Arg Tyr Arg Asn Leu Asn Ile Ala Pro Ala
                165                 170                 175

Glu Asp Gly Tyr Arg Leu Ala Gly Phe Pro Pro Asp His Gln Ala Trp
            180                 185                 190

Arg Glu Glu Pro Trp Ile His His Ala Pro Gln Gly Cys Gly Asn Ser
        195                 200                 205

Ser Arg Thr Ile Thr Gly Asp Thr Cys Asn Glu Glu Thr Gln Asn Leu
    210                 215                 220

Ser Thr Ile Tyr Leu Arg Glu Tyr Gln Ser Lys Val Lys Arg Gln Ile
225                 230                 235                 240

Phe Ser Asp Tyr Gln Ser Glu Val Asp Ile Tyr Asn Arg Ile Arg Asp
                245                 250                 255

Glu Leu Met Asn Lys Val Lys Phe Tyr Val Leu Phe Thr Ala Leu Leu
            260                 265                 270

Ser Ser Leu Cys Ala His Gly Ala Pro Gln Ser Ile Thr Glu Leu Cys
        275                 280                 285

Ser Glu Tyr His Asn Thr Gln Ile Tyr Thr Ile Asn Asp Lys Ile Leu
    290                 295                 300

Ser Tyr Thr Glu Ser Met Ala Gly Lys Arg Glu Met Val Ile Ile Thr
305                 310                 315                 320

Phe Lys Ser Gly Ala Thr Phe Gln Val Glu Val Pro Gly Ser Gln His
                325                 330                 335

Ile Asp Ser Gln Lys Lys Ala Ile Glu Arg Met Lys Asp Thr Leu Arg
            340                 345                 350

Ile Thr Tyr Leu Thr Glu Thr Lys Ile Asp Lys Leu Cys Val Trp Asn
        355                 360                 365

Asn Lys Thr Pro Asn Ser Ile Ala Ala Ile Ser Met Glu Asn
    370                 375                 380

<210> SEQ ID NO 4
<211> LENGTH: 1514
<212> TYPE: DNA
<213> ORGANISM: Escherichia coli

<400> SEQUENCE: 4
ggatccgtgc actctttctt tatcgcttca ctacacattt tatcctcgca tggatgtttt    60
ataaaaaaca tgattgacat catgttgcat ataggttaaa caaaacaagt ggcgttatct   120
ttttccggat tgtcttcttg tatgatatat aagttttcct cgaatgaaaa atataacttt   180 cattttttt attttattag catcgccatt atatgcaaat ggcgacagat tataccgtgc   240
tgactctaga ccccagatg aaataaaacg ttccggaggt cttatgccca gagggcataa   300
tgagtacttc gatagaggaa ctcaaatgaa tattaatctt tatgatcacg cgagaggaac   360
acaaaccggc tttgtcagat atgatgacgg atatgttttcc acttaccttag gtttgagaag   420
```

-continued

```
tgctcactta gcaggacagt ctatattatc aggatattcc acttactata tatatgttat      480
agcgacagca ccaaatatgt ttaatgttaa tgatgtatta ggcgtataca gccctcaccc      540
atatgaacag gaggtttctg cgttaggtgg aataccatat tctcagatat atggatggta      600
tcgtgttaat tttggtgtga ttgatgaacg attacatcgt aacagggaat atagagaccg      660
gtattacaga atctgaata tagctccggc agaggatggt tacagattag caggtttccc      720
accggatcac caagcttgga gagaagaacc ctggattcat catgcaccac aaggttgtgg      780
aaattcatca agaacaatca caggtgatac ttgtaatgag agacccaga atctgagcac      840
aatatatctc agggaatatc aatcaaaagt taagaggcag atattttcag actatcagtc      900
agaggttgac atatataaca gaattcggga tgaattatga ataaagtaaa attttatgtt      960
ttatttacgg cgttactatc ctctctatgt gcacacggag ctcctcagtc tattacagaa     1020
ctatgttcgg aatatcacaa cacacaaata tatacgataa atgacaagat actatcatat     1080
acggaatcga tggcaggcaa agagaaatg gttatcatta catttaagag cggcgcaaca     1140
tttcaggtcg aagtcccggg cagtcaacat atagactccc aaaaaaaagc cattgaaagg     1200
atgaaggaca cattaagaat cacatatctg accgagacca aaattgataa attatgtgta     1260
tggaataata aaaccccaa ttcaattgcg gcaatcagta tggaaaacta gtttgcttta     1320
aaagcatgtc taatgctagg aacctatata acaactactg tacttatact aatgagcctt     1380
atgctgcatt tgaaaaggcg gtagaggatg caataccgat ccttaaactg taacactata     1440
acagcttcca ctacagggag ctgttatagc aaacagaaaa aactaagcta ggctggaggg     1500
gcaagcttgg atcc                                                       1514
```

```
<210> SEQ ID NO 5
<211> LENGTH: 380
<212> TYPE: PRT
<213> ORGANISM: Escherichia coli
<220> FEATURE:
<221> NAME/KEY: SIGNAL
<222> LOCATION: (1)..(18)

<400> SEQUENCE: 5
```

| | | | | | | | | | | | | | | | |
|---|---|---|---|---|---|---|---|---|---|---|---|---|---|---|---|
| Met | Lys | Asn | Ile | Thr | Phe | Ile | Phe | Ile | Leu | Leu | Ala | Ser | Pro | Leu | |
| 1 | | | | 5 | | | | | 10 | | | | | 15 | |
| Tyr | Ala | Asn | Gly | Asp | Arg | Leu | Tyr | Arg | Ala | Asp | Ser | Arg | Pro | Pro | Asp |
| | | | 20 | | | | 25 | | | | | 30 | | | |
| Glu | Ile | Lys | Arg | Ser | Gly | Gly | Leu | Met | Pro | Arg | Gly | His | Asn | Glu | Tyr |
| | | | 35 | | | | 40 | | | | | 45 | | | |
| Phe | Asp | Arg | Gly | Thr | Gln | Met | Asn | Ile | Asn | Leu | Tyr | Asp | His | Ala | Arg |
| | 50 | | | | | 55 | | | | | 60 | | | | |
| Gly | Thr | Gln | Thr | Gly | Phe | Val | Arg | Tyr | Asp | Asp | Gly | Tyr | Val | Ser | Thr |
| 65 | | | | | 70 | | | | | 75 | | | | | 80 |
| Ser | Leu | Ser | Leu | Arg | Ser | Ala | His | Leu | Ala | Gly | Gln | Ser | Ile | Leu | Ser |
| | | | | 85 | | | | | 90 | | | | | 95 | |
| Gly | Tyr | Ser | Thr | Tyr | Tyr | Ile | Tyr | Val | Ile | Ala | Thr | Ala | Pro | Asn | Met |
| | | | 100 | | | | | 105 | | | | | 110 | | |
| Phe | Asn | Val | Asn | Asp | Val | Leu | Gly | Val | Tyr | Ser | Pro | His | Pro | Tyr | Gln |
| | | 115 | | | | | 120 | | | | | 125 | | | |
| Val | Ser | Ala | Leu | Gly | Gly | Ile | Pro | Tyr | Ser | Gln | Ile | Tyr | Gly | Trp | Tyr |
| | 130 | | | | | 135 | | | | | 140 | | | | |
| Arg | Val | Asn | Phe | Gly | Val | Ile | Asp | Glu | Arg | Leu | His | Arg | Asn | Arg | Glu |
| 145 | | | | | 150 | | | | | 155 | | | | | 160 |

```
Tyr Arg Asp Arg Tyr Tyr Arg Asn Leu Asn Ile Ala Pro Ala Glu Asp
            165                 170                 175

Gly Tyr Arg Leu Ala Gly Phe Pro Pro Asp His Gln Ala Trp Arg Glu
            180                 185                 190

Glu Pro Trp Ile His His Ala Pro Gln Gly Cys Gly Asn Ser Ser Arg
            195                 200                 205

Thr Ile Thr Gly Asp Thr Cys Asn Glu Glu Thr Gln Asn Leu Ser Thr
        210                 215                 220

Ile Tyr Leu Arg Glu Tyr Gln Ser Lys Val Lys Arg Gln Ile Phe Ser
225                 230                 235                 240

Asp Tyr Gln Ser Glu Val Asp Ile Tyr Asn Arg Ile Arg Asp Glu Leu
            245                 250                 255

Met Asn Lys Val Lys Phe Tyr Val Leu Phe Thr Ala Leu Leu Ser Ser
            260                 265                 270

Leu Cys Ala His Gly Ala Pro Gln Ser Ile Thr Glu Leu Cys Ser Glu
            275                 280                 285

Tyr His Asn Thr Gln Ile Tyr Thr Ile Asn Asp Lys Ile Leu Ser Tyr
            290                 295                 300

Thr Glu Ser Met Ala Gly Lys Arg Glu Met Val Ile Ile Thr Phe Lys
305                 310                 315                 320

Ser Gly Ala Thr Phe Gln Val Glu Val Pro Gly Ser Gln His Ile Asp
            325                 330                 335

Ser Gln Lys Lys Ala Ile Glu Arg Met Lys Asp Thr Leu Arg Ile Thr
            340                 345                 350

Tyr Leu Thr Glu Thr Lys Ile Asp Lys Leu Cys Val Trp Asn Asn Lys
            355                 360                 365

Thr Pro Asn Ser Ile Ala Ala Ile Ser Met Glu Asn
        370                 375                 380

<210> SEQ ID NO 6
<211> LENGTH: 1508
<212> TYPE: DNA
<213> ORGANISM: Escherichia coli

<400> SEQUENCE: 6
ggatccgtgc actctttctt tatcgcttca ctacacattt tatcctcgca tggatgtttt      60
ataaaaaaca tgattgacat catgttgcat ataggttaaa caaaacaagt ggcgttatct     120
ttttccggat tgtcttcttg tatgatatat aagttttcct cgaatgaaaa atataacttt     180
catttttttt atttattag catcgccatt atatgcaaat ggcgacagat tataccgtgc      240
tgactctaga cccccagatg aaataaaacg ttccggaggt cttatgccca gagggcataa     300
tgagtacttc gatagaggaa ctcaaatgaa tattaatctt tatgatcacg cgagaggaac     360
acaaaccggc tttgtcagat atgatgacgg atatgtttcc acttctctta gtttgagaag     420
tgctcactta gcaggacagt ctatattatc aggatattcc acttactata tatatgttat     480
agcgacagca ccaaatatgt ttaatgttaa tgatgtatta ggcgtataca gccctcaccc     540
atatcaggtt tctgcgttag gtggaatacc atattctcag atatatggat ggtatcgtgt     600
taattttggt gtgattgatg aacgattaca tcgtaacagg gaatatagag accggtatta     660
cagaaatctg aatatagctc cggcagagga tggttacaga ttagcaggtt tcccaccgga     720
tcaccaagct tggagagaag aaccctggat tcatcatgca ccacaaggtt gtggaaattc     780
atcaagaaca atcacaggtg atacttgtaa tgaggagacc cagaatctga gcacaatata     840
```

```
tctcagggaa tatcaatcaa aagttaagag gcagatattt tcagactatc agtcagaggt        900
tgacatatat aacagaattc gggatgaatt atgaataaag taaaatttta tgttttattt        960
acggcgttac tatcctctct atgtgcacac ggagctcctc agtctattac agaactatgt       1020
tcggaatatc acaacacaca aatatatacg ataaatgaca agatactatc atatacggaa       1080
tcgatggcag gcaaaagaga aatggttatc attacattta agagcggcgc aacatttcag       1140
gtcgaagtcc cgggcagtca acatatagac tcccaaaaaa aagccattga aaggatgaag       1200
gacacattaa gaatcacata tctgaccgag accaaaattg ataaattatg tgtatggaat       1260
aataaaaccc ccaattcaat tgcggcaatc agtatggaaa actagtttgc tttaaaagca       1320
tgtctaatgc taggaaccta tataacaact actgtactta tactaatgag ccttatgctg       1380
catttgaaaa ggcggtagag gatgcaatac cgatccttaa actgtaacac tataacagct       1440
tccactacag ggagctgtta tagcaaacag aaaaaactaa gctaggctgg aggggcaagc       1500
ttggatcc                                                                1508
```